United States Patent

Palfreyman et al.

[11] Patent Number: 5,364,853
[45] Date of Patent: Nov. 15, 1994

[54] THIOFORMAMIDE DERIVATIVES

[75] Inventors: Malcolm N. Palfreyman; Nigel Vicker, both of Dagenham, United Kingdom

[73] Assignee: Rhone-Poulenc Rorer Limited, Eastbourne, England

[21] Appl. No.: 867,709

[22] PCT Filed: Jan. 8, 1991

[86] PCT No.: PCT/EP91/00019
§ 371 Date: Aug. 20, 1992
§ 102(e) Date: Aug. 20, 1992

[87] PCT Pub. No.: WO91/10652
PCT Pub. Date: Jul. 25, 1991

[30] Foreign Application Priority Data

Jan. 8, 1990 [GB] United Kingdom ............... 9000342

[51] Int. Cl.$^5$ ............... A61K 31/44; C07D 213/53; C07D 401/12; C07D 411/12
[52] U.S. Cl. ............... 514/332; 514/335; 514/336; 514/339; 514/346; 514/357; 546/265; 546/284; 546/300; 546/331
[58] Field of Search ............... 546/255, 256, 265, 281, 546/284, 300, 331; 514/332, 333, 335, 336, 340, 341, 342, 343, 346, 357, 339

[56] References Cited

FOREIGN PATENT DOCUMENTS 0321274 6/1898 European Pat. Off. .
0321273 6/1989 European Pat. Off. .
0377532 7/1990 European Pat. Off. .
1351024 4/1974 United Kingdom .

*Primary Examiner*—Marianne M. Cintins
*Assistant Examiner*—Phyllis G. Spivack
*Attorney, Agent, or Firm*—Ross J. Oehler

[57] ABSTRACT

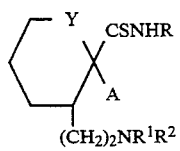

Thioformamide compounds of formula (I) are disclosed in which R is alkyl, Y is methylene, ethylene or a direct bond, A is optionally substituted phenyl or pyridyl, $R^1$ is hydrogen and $R^2$ is N-alkylsulphonyl-, N-phenylsulphonyl-N'-alkylamidino or an arylsulphonyl group; $R^1$ and $R^2$ may both independently represent alkyl- or arylsulphonyl groups.

6 Claims, No Drawings

THIOFORMAMIDE DERIVATIVES

This invention relates to new therapeutically useful thioformamide derivatives, to processes for their preparation and to pharmaceutical compositions containing them.

The thioformamide derivatives of the present invention are those compounds of formula (I), hereinafter depicted wherein: R represents an alkyl group; A represents a phenyl group which is optionally substituted, by one or more substituents selected from, for example, halogen atoms and cyano, nitro, trifluoromethyl, carbamoyl, carboxyl, alkoxycarbonyl and alkylsulphonyl groups or, preferably, a heterocyclyl group, preferably selected from quinolin-3-yl, isoquinolin-4-yl, pyridazin-4-yl, pyrimidin-5-yl, pyrazin-3-yl, indol-3-yl, thiazol-5-yl, and, more especially, pyridyl, e.g. pyrid-3-yl or pyrid-4-yl, optionally substituted by an alkyl or alkoxy group, or by a halogen atom; Y represents a direct bond or an ethylene or, preferably, methylene group; and either:

(1) $R^1$ represents hydrogen and $R^2$ represents:

i) a group of formula —$CXNHR^3$, wherein $R^3$ is an alkyl group and X is a group of formula =$NSO_2R^4$, wherein $R^4$ is alkyl or phenyl; or ii) a group of formula —$SO_2R^5$, wherein $R^5$ represents:

a) a naphthyl or phenyl group optionally substituted by one or more halogen atoms, hydroxy, alkoxy, $C_{3-6}$ cycloalkoxy, alkyl, $C_{2-4}$ alkenyl, cyano, nitro, trifluoromethyl, carboxy, alkoxycarbonyl, amino, alkylamino, dialkylamino, alkoxycarbonylamino, alkanoylamino, dialkanoylamino, benzoylamino, carbamoyl, N-(optionally hydroxyalkyl)carbamoyl or N,N-di(optionally hydroxyalkyl)carbamoyl groups, or amino or carbamoyl groups N,N-disubstituted by a $C_{3-6}$ alkylene chain one or more of whose methylene groups may have been replaced by an oxygen or sulphur atom or by an imino or alkylimino group;

b) a pyridyl or thienyl group; or c) an alkyl group optionally substituted by one or more halogen atoms, phenyl, naphthyl, pyridyl, hydroxy, alkoxy, $C_{3-6}$ cycloalkoxy, alkyl, $C_{2-4}$ alkenyl, cyano, nitro, trifluoromethyl, carboxy, alkoxycarbonyl, amino alkylamino, dialkylamino, alkoxycarbonylamino, alkanoylamino, dialkanoylamino, benzoylamino, carbamoyl, N-(optionally hydroxyalkyl)carbamoyl or N,N-di(optionally hydroxyalkyl)carbamoyl groups, or amino or carbamoyl groups N,N-disubstituted by a $C_{3-6}$ alkylene chain, one or more of whose methylene groups may have been replaced by an oxygen or sulphur atom or an imino or alkylimino group;

(2) $R^1$ and $R^2$ both independently represent a group of formula —$SO_2R^5$, as defined above; or (3) $R^1$ and $R^2$ together with the nitrogen to which they are attached from a group of formula (IA) wherein each group $R^9$ is independently hydrogen or alkyl and Q is oxygen, sulphur or a group of formula $NR^9$ or $(CH_2^9)_n$, wherein n is 0, 1 or 2;

wherein all alkyl groups and moieties, including those in alkoxy, alkoxycarbonyl and alkanoyl groups, are straight-chain or branched, and, unless otherwise specified, contain one to about six carbon atoms; and salts thereof.

Particularly important classes of compounds of formula (I) exhibit one or more of the following features:
i) R represents a methyl or ethyl group;
ii) A represents a pyrid-3-yl or pyrid-4-yl group;
iii) Y represents a methylene group;
iv) $R_1$ represents a hydrogen atom;
v) $R^3$ represents a methyl group;
vi) $R^4$ represents a methyl or phenyl group;
vii) $R^5$ represents:

a) a phenyl or naphthyl (especially 1-naphthyl) group optionally substituted by one or more halogen (especially fluorine or chlorine) atoms or nitro, cyano, alkoxy (especially methoxy) or dialkylamino (especially dimethylamino) groups;

b) a pyrid-3-yl or thien-2-yl group; or c) an alkyl group of up to 4 carbon atoms; and/or viii) the group of formula (IA) is a 3,5-dioxomorpholino group; the other symbols being as hereinbefore defined, and their pharmaceutically acceptable salts.

The presence of an axocyclic aminoethyl group on the ring creates an isomeric centre in the molecule which in association with the adjacent asymmetric ring carbon atom leads to 4 stereoisomers which, optionally, can be separated into 2 racemic pairs. The racemic pair and enantiomers in which the —$(CH_2)_2NR^1R^2$ and —CSNHR groups are in the trans relationship are preferred. In certain cases the substituents A, R, $R^1$ and $R^2$ can also contribute to stereoisomerism. All such forms are embraced by the present invention.

Particularly important compounds of the present invention include the following:

1H (±)-trans-2-(N-methyl-N'-benzenesulphonyliminoureido)ethyl-N-methyl-1-(3-pyridyl)cyclohexane carbothioamide 1I (±)-trans-2-(N-methyl-N'-methanesulphonyliminoureido)ethyl-N-methyl-1-(3-pyridyl)-cyclohexane carbothioamide 1J (±)-trans-2-benzenesulphonylaminoethyl-N-methyl-1-(3-pyridyl)cyclohexane carbothioamide 1K (±)-trans-2-methanesulphonylaminoethyl-N-methyl-1-(3-pyridyl)cyclohexane carbothioamide 1L (±)-trans-2-(4-fluorobenzenesulphonyl)aminoethyl-N-methyl-1-(3-pyridyl)cyclohexane carbothioamide 1M (±)-trans-2-(4-nitrobenzenesulphonyl)aminoethyl-N-methyl-1-(3-pyridyl)cyclohexane carbothioamide 1N (±)-trans-2-(4-chlorobenzenesulphonyl)aminoethyl-N-methyl-1-(3-pyridyl)cyclohexane carbothioamide 1O (±)-trans-2-(4-methoxybenzenesulphonyl)aminoethyl-N-methyl-1-(3-pyridyl)cyclohexane carbothioamide 1P (±)-trans-2-(2-thiophenesulphonyl)aminoethyl-N-methyl-1-(3-pyridyl)cyclohexane carbothioamide 1Q (±)-trans-2-(3-pyridinesulphonyl)aminoethyl-N-methyl-1-(3-pyridyl)cyclohexane carbothioamide 1R (±)-trans-2-(3,4-difluorobenzenesulphonyl)aminoethyl-N-methyl-1-(3-pyridyl)cyclohexane carbothioamide 1S (±)-trans-2-(5-dimethylamino-1-naphthalenesulphonyl)aminoethyl-N-methyl-1-(3-pyridyl)cyclohexane carbothioamide 1T (±)-trans-2-(3,5-dioxomorpholino)ethyl-N-methyl-1-(3-pyridyl)cyclohexane carbothioamide 2A (±) trans-2-(propylsulphonyl)aminoethyl-N-methyl-1-(3-pyridyl)cyclohexane carbothioamide 2B (±)-trans-2-(isopropylsulphonyl)aminoethyl-N-methyl-1-(3-pyridyl)cyclohexane carbothioamide 2C (±)-trans-2-(butylsulphonyl)aminoethyl-N-methyl-1-(3-pyridyl)cyclohexane carbothioamide 2D (±)-trans-2-(fluorobenzenesulphonyl)aminoethyl-N-methyl-1-(3-pyridyl)cyclohexane carbothioamide
2E (±)-trans-2-(3-cyanobenzenesulphonyl)aminoethyl-N-methyl-1-(3-pyridyl)cyclohexane carbothioamide
2F (±)-trans-2-(3-benzenesulphonyl)aminomethyl-N-methyl-1-(3-pyridyl)cyclohexane carbothioamide
2G (±)-trans-2-(isopropylsulphonyl)aminoethyl-N-methyl-1-(3-pyridyl)cyclohexane carbothioamide
2H (±)-trans-2-(4-fluorobenzenesulphonyl)aminoethyl-N-ethyl-1-(3-pyridyl)cyclohexane carbothioamide
2I (±)-trans-2-(3-pyridinesulphonylaminoethyl-N-ethyl-1-(3-pyridyl)cyclohexane carbothioamide
2J (−)-trans-2-(3-pyridinesulphonyl)aminoethyl-N-methyl-1-(3-pyridyl)cyclohexane carbothioamide
2K (−)-trans-2-(4-fluorobenzenesulphonyl)aminoethyl-N-methyl-1-(3-pyridyl)cyclohexane carbothioamide
2L (−)-trans-2-(isopropylsulphonyl)aminoethyl-N-methyl-1-(3-pyridyl)cyclohexane carbothioamide
2M (±)-trans-2-(isopropylsulphonyl)aminoethyl-N-methyl-1-(4-pyridyl)cyclohexane carbothioamide as well as their stereoisomeric forms and pharmaceutically acceptable salts thereof.

Letters 1H to 1T and 2A to 2M are allocated to compounds for ease of reference in other parts of the specification.

Compounds within the scope of the present invention exhibit positive pharmacological activities as demonstrated by tests which are believed to correlate to pharmacological activity in humans and other animals.

For example, the compounds have valuable pharmacological properties, in particular properties which are indicative of utility in the treatment and/or prophylaxis of disorders associated with:

(1) vascular smooth muscle contraction including hypertension and other cardiovascular disorders such as congestive heart failure, and conditions associated with tissue ischaemia such as angina, peripheral vascular disease and cerebrovascular disease;

(2) respiratory smooth muscle contraction including reversible airways obstruction and asthma;

(3) contraction of smooth muscle of gastrointestinal tract, urinary bladder and uterus, including peptic ulcers, irritable bowel syndrome and diverticular disease; irritable bladder syndrome; and premature labour.

For example, compounds of general formula (I) were submitted to:

Vaso-relaxant Activity Tests.

The test methods used were adapted from those described by Winslow et al [Eur.J.Pharmacol., 131, 219–228 (1986)] and Karaki [J.Pharmacol. Methods, 18, 1–21 (1987)] for differentiating vaso-relaxant activity.

Test A: Activity against contractions induced by low K+ concentrations in the isolated rat aorta Thoracic aorta was removed from rats and transverse strips, denuded of endothelium, were suspended in a bath containing Krebs solution. The tension was recorded and a contraction induced by addition of 20 mM K+ (potassium ion) to the bathing solution. The test compound was added to the bath as a solution in increasing cumulative concentration. The concentration in the bathing solution of the test compound which reduced the K+-induced contraction by 90% was determined and expressed in μM as the effective concentration (EC$_{90}$), given in Table 1.

TABLE 1

| Compound | Activity Test A EC$_{90}$ μM |
|---|---|
| 1H | 0.3 |
| 1I | 0.03 |
| 1J | 0.0003 |
| 1K | 0.17 |
| 1L | 0.007 |
| 1M | 0.3 |
| 1N | 0.03 |
| 1O | 0.3 |
| 1P | 0.001 |
| 1Q | 0.03 |
| 1R | 0.01 |
| 1S | 1 |
| 1T | 1 |

Test B: Activity against contractions induced by high K+ concentrations in isolated rat aorta The test method was as in Test A with the exception that contractions were induced by addition of 60 mM K+ to the bathing solution. The cumulative addition of the solutions of the test compound was conducted and the concentration in the bath reducing the K+-induced contraction by 90% was found and expressed as the EC$_{90}$. For each compound tested it was greater than 30 μM.

The compounds of general formula (I) can be prepared by the application and adaptation of known methods, for example as hereinafter identified.

By the term "known methods" as used in this specification is meant methods heretofore used or described in the literature.

According to a feature of the present invention, compounds of formula (I), wherein R$^1$ is hydrogen and R$^2$ is a group of formula —C(=NSO$_2$R$^4$)NHR$^3$, as hereinbefore defined, are prepared by the reaction of compounds of formula (V), hereinafter depicted, wherein R, Y, A and R$^4$ are as hereinbefore defined, with a compound of general formula:

R$^3$NH$_2$ (VI)

wherein R$^3$ is as hereinbefore defined. The reaction is carried out in a inert organic solvent e.g. ethanol at a temperature of from 0° C. to 80° C., preferably at reflux.

According to a further feature of the invention compounds of formula (I), wherein R, A and Y are as hereinbefore defined and one or both of R$^1$ and R$^2$ represents a group —SO$_2$R$_5$, as hereinbefore defined, are synthesized from compounds of formula (I) wherein one of R$^1$ and R$^2$ is hydrogen, or from a compound of formula (II), wherein Y, A and R are as hereinbefore defined, by reaction with a compound of formula:

R$^2$SO$_2$Cl (VIII)

wherein R$^5$ is as hereinbefore defined, in the presence of an anhydrous inert organic solvent e.g. dichloromethane or tetrahydrofuran. The reaction is effected, optionally in the presence of an acid acceptor, for example a teritary amine, e.g. triethylamine, or an inorganic base, e.g. sodium bicarbonate, at a temperature of from −30° C. to +30° C.

According to a further feature of the invention, compounds of formula (I), wherein R$^1$ and R$^2$ form part of a ring of formula (IA) and R, A and Y are as hereinbefore defined, are synthesized from compounds of formula (II), wherein Y, A and R are as hereinbefore defined, by reaction with a compound of formula (IX) wherein Q and $R^9$ are as hereinbefore defined. The reaction is preferentially carried out in an inert organic solvent e.g. toluene, at reflux, in the presence of 1,2-dichlorobenzene to aid solubility.

The intermediate compounds and the starting materials may be prepared by the application or adaptation of known methods, for example as indicated in the following Examples and Reference Examples.

For example, compounds of formula (V) can be synthesised from compounds of formula (II), hereinafter depicted, wherein Y, A and R are as hereinbefore defined, by reaction with a compound of formula:

$$(CH_3S)_2C=NSO_2R^4 \qquad \text{(VII)}$$

wherein $R^4$ is as hereinbefore defined. The reaction is carried out in a inert organic solvent e.g. ethanol at a temperature of from 0° C. to 80° C.

Compounds of formula (II), wherein A, Y and R are as hereinbefore defined, can be prepared from the corresponding compounds of formula (X), hereinafter depicted, wherein A, Y and R are as hereinbefore defined, by reduction with a complex metal reducing agent, such as an aluminium hydride (e.g. lithium aluminium hydride) in a dry organic solvent, such as an ether (e.g. tetrahydrofuran) at elevated temperature, preferably from 40° to 80° C.

Compounds of formula (X), wherein A, Y and R are as hereinbefore defined, may be prepared by the reduction of the corresponding compounds of general formula (XI), with a complex metal reducing agent, such as an aluminium hydride (e.g. lithium aluminium hydride) in a dry inert organic solvent, such as an ether (e.g. tetrahydrofuran) at room temperature This reaction preferentially gives the reduced product (K) in which the —CSNHR group bears a trans relationship to the —CH₂CN group.

The compounds of formula (XI), wherein Y, A and R are as hereinbefore defined, may be prepared by the reaction of a compound of general formula (XII), hereinafter depicted, wherein A, Y and R are as hereinbefore defined, with a compound of general formula:

$$(R^6O)_2P(O)CH_2CN \qquad \text{(XIII)}$$

wherein $R^6$ represents an alkyl group of 1 to 4 carbon atoms, preferably a methyl or ethyl group. The reaction is generally carried out in the presence of a base, preferably sodium hydride, in an ethereal solvent (e.g. tetrahydrofuran) and preferably at a temperature of from 20° C. to 100° C.

Compounds of general formula (XII), wherein A, Y and R are as hereinbefore defined may be prepared by the reaction of a compound of general formula (XIV), hereinafter depicted, wherein A and Y are as hereinbefore defined, with a compound of the general formula:

$$R—N=C=S \qquad \text{(XV)}$$

wherein R is as hereinbefore defined. The reaction is generally carried out in an anhydrous inert organic solvent such as tetrahydrofuran, dimethylformamide or hexamethylphosphoramide, or a mixture of these solvents, at a temperature from −80° C. to +50° C., in the presence of an inorganic base such as potassium tert.-butoxide, or an organo-lithium derivative such as n-butyllithium, or of sodium hydride.

Compounds of formula (XIV), wherein A is as hereinbefore defined in Y is a methylene or ethylene group, can be made via a dehydrobromination/rearrangement reaction of compounds of formula (XVIII), hereinafter depicted, wherein A is as defined above and $Y^1$ is methylene or ethylene. This may be initiated by a bromido extracting agent such as a silver salt (e.g. silver perchlorate) and carried out in an inert anhydrous solvent (for example an ether such as tetrahydrofuran).

Compounds of formula (XVIII), wherein A and $Y^1$ are as defined above, can be made by the addition of hypobromous acid across the double bond of compounds of formula (XIX), hereinafter depicted, wherein A and $Y^1$ are as defined above. This may be done by reaction with a brominating agent (e.g. 1,3-dibromo-5,5-dimethylhydantoin) in an aqueous acidic medium, optionally in the presence of a cosolvent.

Compounds of formula (XIX), wherein A and $Y^1$ are as defined above, can be made via a coupling reaction between a compound of formula (XX), hereinafter depicted, (typically made in situ by the reaction of a compound of formula (XXI), hereinafter depicted, wherein $Y^1$ is as defined above and $R^8$ and Z are conventional groups present in a Wittig reagent and its phosphonium salt precursor [e.g. phenyl and bromine respectively] with a strong base, such as potassium t-butoxide, in an anhydrous solvent, such as tetrahydrofuran, preferably under an inert atmosphere) and a compound of formula:

$$A-CHO \qquad \text{(XXII)}$$

wherein A is as defined above.

Alternatively, compounds of formula (XIV), wherein A and Y are as hereinbefore defined, can be made from compounds of formula (XXIII), wherein A and Y are as defined above. This is typically carried out in the presence of a strongly acidic agent (e.g. phosphorus pentoxide or sulphuric acid), optionally in a solvent (such as toluene) and at elevated temperature.

Compounds of formula (XXIII) can be made by reaction of a compound of formula:

$$A-Hal \qquad \text{(XXV)}$$

wherein A is as defined above and Hal is a halogen, preferably bromine or chlorine atom, in the presence of a strong base, such as an alkyl lithium (e.g. butyllithium), with a compound of formula (XXIV), wherein Y is as defined above, in an inert solvent such as an ether (e.g. diethyl ether) or a hydrocarbon (e.g. toluene).

Alternatively, compounds of general formula (XII), wherein A and Y are as hereinbefore defined and R is methyl, can be prepared from compounds of general formula (XVI), wherein A and Y are as defined above and $R^7$ is an alkyl group of 1 to 4 carbon atoms or a benzyl or carboxymethyl radical, by reaction with methylamine. The reaction is generally carried out with an excess of amine, without a solvent or in an inert organic solvent such as an ether (e.g. tetrahydrofuran) an aromatic hydrocarbon or an alcohol or a mixture of these solvents at a temperature from room temperature to 130° C., optionally under pressure, and the amine may be added in an alcoholic solution, preferably ethanol.

It may be advantageous for the thiol formed during the reaction to be fixed in the form of a heavy metal salt using a thiol acceptor such as mercuric chloride.

Compounds of formula (XVI), wherein Y, A and $R^7$ are as hereinbefore defined may be prepared by the reaction of compounds of formula (XIV), wherein Y and A are as hereinbefore defined, with carbon disulphide followed by reaction with a compound of formula:

R⁷-X (XVII)

wherein R⁷ is as hereinbefore defined and X is halogen, preferably chlorine, bromine or iodine, or a readily displaceable ester group such as methanesulphonyloxy or 4-toluenesulphonyloxy. The reaction is generally carried out in an anhydrous inert organic solvent such as tetrahydrofuran, to which hexamethylphosphoramide may be added, at a temperature from −80° C. to +50° C. in the presence of an organic base such as potassium tert.-butoxide, or an organo-lithium derivative such as butyllithium, or sodium hydride.

By the term "pharmaceutically acceptable salts" as used in this specification is meant salts the anions or cations of which are relatively innocuous to the animal organism when used in therapeutic doses so the the beneficial pharmaceutical properties of the parent compounds of general formula (I) capable of forming salts are not vitiated by side-effects ascribable to those anions or cations.

It is to be understood that, where in this specification reference is made to compounds of formula (I), it is intended to refer also, where the context so permits, to their pharmaceutically acceptable salts.

Suitable acid addition salts for use in pharmaceuticals may be selected from salts derived from inorganic acids, for example hydrochlorides, hydrobromides, phosphates, sulphates and nitrates, and organic acids, for example oxalates, lactates, tartrates, acetates, salicylates, citrates, propionates, succinates, fumarates, maleates, methylene-bis-β-hydroxynaphthoates, gentisates and di-p-toluoyltartrates.

Suitable salts with bases include alkali metal (e.g. sodium and potassium), alkaline earth metal (e.g. calcium and magnesium), ammonium and amine (e.g. diethanolamine, triethanolamine, octylamine, morpholine and dioctylmenthylamine) salts.

As well as being useful in themselves as active compounds, salts of the compounds of general formula (I) capable of forming salts with acids or bases are useful for the purposes of purification of the parent compounds of general formula (I), for example by exploitation of the solubility differences between the salts and the parent compounds, by techniques well known to those skilled in the art.

The thioformamide derivatives of general formula (I) obtained by the aforedescribed processes can be purified by the usual physical methods, in particular crystallisation and chromatography especially to resolve mixtures of enantiomers using a chiral column.

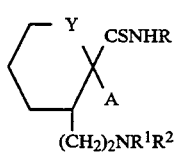
(I)

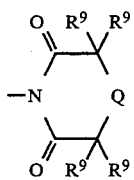
(IA)

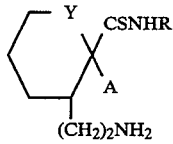
(II)

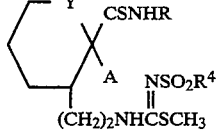
(V)

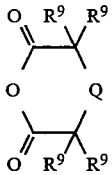
(IX)

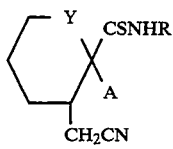
(X)

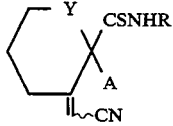
(XI)

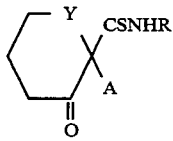
(XII)

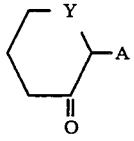
(XIV)

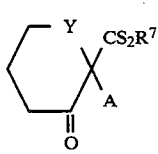
(XVI)

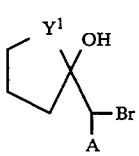
(XVIII)

-continued

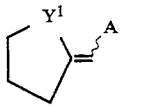

(XIX)

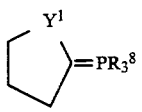

(XX)

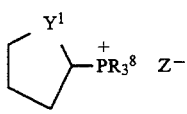

(XXI)

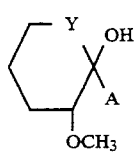

(XXIII)

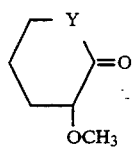

(XXIV)

The following Examples and Reference Examples illustrate the preparation of compounds according to the present invention and their intermediates.

All N.M.R. spectra were recorded at 200 MHz. The chemical shifts are expressed in ppm relative to tetramethylsilane. Abbreviations in the text are as follows:

s=singlet, d=doublet, t=triplet, q=quartet, dd=doublet of doublets, ddd=doublet of doublets of doublets, dt=doublet of triplets, dq=doublet of quartets, m=multiplet, c=unresolved complex peak, br=broad single.

The expression "m/z" indicates the peak assigned to the molecular ion in the mass spectrum.

EXAMPLE 1

Compound 1H

To a solution of (±)-trans-2(2-(N-benzenesulphonyl-S-methylisothioureido)ethyl)-N-methyl-1-(3-pyridyl)-cyclohexane carbothioamide (280 mg, 0.57 mmol) in ethanol (5 ml) was added a 33% ethanolic solution of methylamine (1 ml) and the mixture heated at reflux for 6 hr, cooled and concentrated in vacuo to give a pale yellow oil. The oil was purified by flash chromatography over silica gel using ethyl acetate/methanol (9:1) as eluent to give (±)-trans-2-(N-methyl-N'-benzenesulphonyliminoureido)ethyl-N-methyl-1-(3-pyridyl)cyclohexane carbothioamide (100 mg), as a white solid, m.p. 163°–164° C.;

[N.M.R.(CDCl$_3$): 1.0–1.6 (m,5H), 1.6 (m,1H), 1.8–2.0 (m,2H), 2.8 (t, 3H), 2.9–3.0 (m,2H), 3.05(t, 3H), 3.1–3.2 (m, 2H), 7.2 (q, 1H), 7.4 (m, 3H), 7.8 (d, 3H), 8.4 (d, 1H), 8.6 (d,1H), 8.8 (br s, 1H)

Found C, 57.7; H,6.6; N, 14.4; S, 13.3%

C$_{23}$H$_{31}$N$_5$O$_2$S$_2$ requires C, 58.3; H, 6.6; N, 14.8; S, 13.5%].

EXAMPLE 2

Compound 1I

To a solution of (±)-trans-2-(2-(N-methanesulphonyl-S-methylisothioureido)ethyl)-N-methyl-1-(3-pyridyl)cyclohexane carbothioamide (220 mg, 0.5 mmol) in ethanol (5 ml) was added a 33% solution of methylamine in ethanol (1 ml) and the solution heated at reflux for 5 hr. After cooling, the solution was concentrated in vacuo to give a light brown oil. The oil was purified by flash chromatography over silica gel using ethyl acetate/methanol (95:5) as eluent to give (±)-trans-2-(N-methyl-N'-methanesulphonyliminoureido)ethyl-N-methyl-1-(3-pyridyl)-cyclohexane carbothioamide (100 mg), m.pt 125°–126° C.;

[N.M.R. (CDCl$_3$): 1.3–1.7 (m,7H), 1.75 (m,1H), 2.15 (m, 1H), 2.6 (m, 1H), 2.9(d, 3), 2.95 (m,1H), 2.96 (s, 3H), 3.1 (d, 3H), 3.25 (m,2H), 7.33 (q, 1H), 7.4 (br s, 1H), 7.8(dt, 1H), 8.55 (dd, 1H), 8.65 (d, 1H)

Found: C, 51.4; H, 7.2; N, 16.65; S, 15.25%

C$_{18}$H$_{29}$N$_5$O$_2$S$_2$.½H$_2$O requires: C, 52.5; H,7.1; N, 17.0; S, 15.6%].

EXAMPLE 3

Compounds 1J to 1S

To a solution of (±)-trans-2-aminoethyl-N-methyl-1-(3-pyridyl)cyclohexane carbothioamide (0.5 g, 1.8 mmol) in dichloromethane (10 ml) at 0° C. was added, with stirring, triethylamine (0.25 ml, 1.8 mmol) and then benzenesulphonyl chloride (0.22 ml, 1.8 mmol). After stirring for 1 hr at 0° C., the solution was allowed to warm slowly to room temperature and stirred for a further 1 hr. The solution was treated with water (30 ml) and dichloromethane (30 ml). The organic layer was collected, washed with water, dried (MgSO$_4$) and concentrated in vacuo to give an orange solid. The residue was subjected to flash chromatography over silica gel using methanol/ethyl acetate (5:95) as eluent, to give (±)-trans-2-benzenesulphonylaminoethyl-N-methyl-1-(3-pyridyl)cyclohexane carbothioamide (130 mg), m.pt 109°–110° C.;

[N.M.R.(CDCl$_3$): 1.25–1.55 (m, 6H), 1.8(m,1H), 2.1–2.2 (m,2H), 2.5, (m, 1H), 2.8 (m, 2H), 3.0 (m, 1H), 3.1(d, 3H), 4.9 (br t, 1H), 7.2 (br s, 1H), 7.3(q, 1H), 7.5–7.6 (m, 3H), 7.8 (dt, 1H), 7.85(d,2H), 8.5 (dd, 1H), 8.6 (d, 1H)

Found: C, 60.3; H, 6.76; N, 9.8%

C$_{21}$H$_{27}$N$_3$O$_2$S$_2$ requires: C, 60.4; H, 6.5; N, 10.1%].

By proceeding in a similar manner but replacing the benzenesulphonyl chloride with the appropriate sulphonyl chloride, there were prepared:

i)(±)-trans-2-methanesulphonylaminoethyl-N-methyl-1-(3-pyridyl)cyclohexane carbothioamide, m.pt 90° C.;

[N.M.R. (CDCl$_3$): 1.3–1.4(m,1H), 1.4–1.7(m,6H), 1.9–2.05(m, 1H), 2.1–2.2(m,1H) 2.6–2.7(m,1H), 2.9(s, 3H), 3.0–3.1 (m, 2H), 3.1(d, 3H), 3.2(m, 1H), 4.8 (br t, 1H), 7.3 (q, 1H),7.5 (br s, 1H), 7.85 (dt, 1H), 8.5 (dd, 1H), 8.65 (d, 1H)

Found: C, 53.6; H, 7.2; N, 11.1; S, 17.0%

C$_{16}$H$_{25}$N$_3$O$_2$S$_2$ requires: C, 54.0; H, 7.1; N, 11.8; S, 18.0%];

ii) (±)-trans-2-(4-fluorobenzenesulphonyl)-aminoethyl-N-methyl-1-(3-pyridyl)cyclohexane carbothioamide, m.pt. 64°–66° C.;

[N.M.R.(CDCl$_3$): 1.2–1.9(m,7H), 2.1 (m,1H), 2.55 (m,1H), 2.7–3.0 (m, 4H), 3.1(d, 3H), 5.2 (br t, 1H), 7.1–7.3 (m, 3H), 7.4 (br s, 1H), 7.7–7.9 (m, 3H) 8.4 (dd, 1H), 8.6 (d, 1H)

Found: C, 57.9; H, 6.3; N, 9.1; S, 14.2%

$C_{21}H_{26}FN_3O_2S_2$ requires: C, 57.9; H, 6.0: N, 9.65; S, 14.7%];

iii) (±)-trans-2-(4-nitrobenzenesulphonyl)aminoethyl-N-methyl-1-(3-pyridyl)cyclohexane carbothioamide, m.pt 108°–109° C.

[N.M.R.(CDCl$_3$): 1.2–1.9(m,8H), 2.0–2.2 (m, 1H), 2.4–2.6 (m, 1H), 2.7–3.0 (m, 3H), 3.1 (d,3H), 5.8 (br t, 1H), 7.2–7.4 (m, 2H), 7.8 (d,1H), 8.0 (d, 2H), 8.4 (dd, 3H), 8.6(d, 1H)

Found: C, 54.2; H, 5.6; N, 11.8; S, 13.8%

$C_{21}H_{26}N_4O_4S_2$ requires: C, 54.3; H, 5.7; N, 12.1; S, 13.9%];

iv) (±)-trans-2-(4-chlorobenzenesulphonyl)aminoethyl-N-methyl-1-(3-pyridyl)cyclohexane carbothioamide, mpt 106°–107° C.;

[N.M.R.(CDCl$_3$): 1.3–1.6 (m, 7H), 1.8 (m,1H), 2.1–2.2(m,1H), 2.5–2.55(m,1H), 2.75–2.9(m, 2H), 2.95–3.05(m, 1H), 3.1 (d, 3H), 5.1 (br s, 1H),7.25(br s, 1H), 7.3 (q, 1H), 7.5(d, 2H), 7.8 (m, 3H), 8.5 (dd, 1H), 8.65 (d, 1H)

Found: C, 55.3; H, 5.8; N, 9.2; S, 13.9%

$C_{21}H_{26}ClN_3O_2S_2$ requires: C, 55.8; H, 5.8; N, 9.3; S, 14.2%];

v) (±)-trans-2-(4-methoxybenzenesulphonyl)-aminomethyl-N-methyl-1-(3-pyridylcyclohexane carbothioamide, m.pt 95°–96° C.;

[N.M.R.(CDCl$_3$): 1.25–1.6 (m,7H), 1.8 (m,1H), 2.05–2.15(m, 1H), 2.52–2.6(m, 1H), 2.8–2.9 (m, 2H), 2.9–3.0(m, 1H), 3.1 (d, 3H), 3.9 (s, 3H),4.85 (br t, 1H), 7.0(d, 2H), 7.25–7.35 (m, 3H), 7.8(d, 2H), 8.5 (dd, 1H), 8.6 (d, 1H)

Found: C, 59.5; H, 6.7; N, 9.5; S, 14.0%

$C_{22}H_{29}N_3O_3S_2$ requires: C, 59.0; H, 6.5; N, 9.4: S, 14.3%];

vi) (±)-trans-2-(2-thiophenesulphonyl)aminoethyl-N-methyl-1-(3-pyridyl)cyclohexane carbothioamide, m.pt 96°–98° C.;

[N.M.R.(CDCl$_3$): 1.3–1.6 (m,7H), 1.8–1.9(m, 1H), 2.1–2.15 (m, 1H), 2.5–2.6 (m, 1H), 2.8–2.9 (m, 1H), 2.9–3.0 (m, 1H), 3.0–3.1 (m, 1H), 3.1(d, 3H), 5.15 (br t, 1H), 7.1 (dd, 1H), 7.3 (q, 1H), 7.32 (br s, 1H), 7.6 (m, 2H), 7.8 (dt, 1H), 8.5 (dd, 1H), 8.65 (dd)

Found: C, 53.6; H, 5.9; N, 9.6%

$C_{19}H_{25}N_3O_2S_3$ requires: C, 53.9; H, 5.95; N, 9.9%];

vii) (±)-trans-2-(3-pyridinesulphonyl)aminoethyl-N-methyl-1-(3-pyridyl)cyclohexane carbothioamide, m.pt 101°–102° C.;

[N.M.R. (CDCl$_3$): 1.3–1.6 (m, 7H), 1.8–1.9(m, 1H), 2.1–2.15 (m, 1H), 2.5–2.6 (m, 1H), 2.8–2.9 (m, 2H), 3.05(m, 1H), 3.1(d, 3H), 5.9(br t, 1H), 7.3 (q, 1H), 7.45 (q, 1H), 7.5 (br s, 1H), 7.8 (dt, 1H), 8.15 (dt, 1H), 8.4 (dd, 1H), 8.6(d, 1H), 8.8(dd, 1H), 9.0 (d, 1H)

Found C, 55.9; H, 6.3; N, 13.1%

$C_{20}H_{26}N_4O_2S_2.\frac{1}{2}H_2O$ requires: C, 56.1; H, 6.36; N, 13.1%];

viii) (±)-trans-2-(3,4-difluorobenzenesulphonyl)aminoethyl-N-methyl-1-(3-pyridyl)cyclohexane carbothioamide, m.pt. 90°–91° C.;

[N.M.R.(CDCl$_3$): 1.2–1.6 (m, 6H), 1.6–2.0(m, 3H), 2.0–2.2(m, 1H), 2.4–2.6 (m, 1H), 2.7–3.1 (m, 2H), 3.1 (d, 3H), 5.5 (t, 1H), 7.2–7.4 (m, 2H), 7.6–7.8 (m, 2H), 8.45 (dd, 1H), 8.6(d, 1H)

Found: C, 55.6; H, 5.6; N, 9.0; S, 14.5%

$C_{21}H_{25}F_2N_3O_2S_2$ requires: C, 55.6; N, 5.6; N, 9.3; S, 14.1%]; and ix) (±)-trans-2-(5-dimethylamino-1-naphthalenesulphonyl)aminoethyl-N-methyl-1-(3-pyridyl)cyclohexane carbothioamide, m.pt 125°–126° C.

[N.M.R. (CDCl$_3$): 1.0–1.4 (m, 6H), 1.4–1.6 (m, 2H), 1.9–2.1 (m, 1H), 2.3–2.5 (m, 1H), 2.6–2.8 (m, 2H), 2.85 (s, 6H), 2.9 (m, 1H), 3.1 (d, 1H), 5.2 (br t, 1H), 7.1–7.3 (m, 4H), 7.4–7.7 (m, 3H), 8.2–8.4 (dd, 2H), 8.4–8.5 (m, 2H)

Found: C, 60.3; H, 6.7; N, 9.8%

$C_{27}H_{34}N_4O_2S_2$ requires: C, 63.5; H, 6.7; N, 11.0%].

EXAMPLE 4

Compound 1T

To a solution of (±)-trans-2-aminoethyl-N-methyl-1-(3-pyridyl)cyclohexane carbothioamide (1 g, 3.6 mmol) in toluene (20 ml) and 1,2-dichlorobenzene (5 ml) was added 90% diglycollic anhydride (928 mg, 7.2 mmol) and the solution heated at reflux for 3 hr. After this time the mixture was cooled and the liquors decanted from the black tar and concentrated in vacuo to give a pale yellow oil. The oil was subjected to flash chromatography over silica gel using methanol/ethyl acetate (5:95) as eluent to give (±)-trans-2-(3,5-dioxomorpholino)ethyl-N-methyl-1-(3-pyridyl)cyclohexane carbothioamide (290 mg), as a cream solid, m.pt 181°–183° C.

[N.M.R. (CDCl$_3$):1.4–1.6 (m, 8H), 2.0–2.2 (m, 2H), 2.6–2.7 (m, 1H), 3.1(d, 3H),3.7 (m, 1H), 3.8 (m, 1H), 4.35 (s, 4H), 7.3 (br s, 1H), 7.4 (q, 1H), 7.95 (d, 1H), 8.55 (dd, 1H), 8.6 (d, 1H)

Found: C, 60.2; H, 6.6; N, 11.1; S, 7.3%

$C_{19}H_{25}N_3O_3S$ requires: C, 60.8; H, 6.7; N, 11.2; S, 8.5%].

EXAMPLE 5

Compounds 2A to 2M

By carrying out processes similar to those described herein, more especially in the Examples and Reference Examples, there were prepared the following compounds:

(±) trans-2-(propylsulphonyl)aminoethyl-N-methyl-1-(3-pyridyl)cyclohexane carbothioamide, m.p. 81°–83° C., in the form of a foam;

(±)-trans-2-(isopropylsulphonyl)aminoethyl-N-methyl-1-(3-pyridyl)cyclohexane carbothioamide, m.p. 104°–106° C.;

(±)-trans-2-(butylsulphonyl)aminoethyl-N-methyl-1-(3-pyridyl)cyclohexane carbothioamide, m.p. 82°–84° C., in the form of a foam;

(±)-trans-2-(fluorobenzenesulphonyl)aminoethyl-N-methyl-1-(3-pyridyl)cyclohexane carbothioamide, m.p. 105°–112° C., in the form of a foam;

(±)-trans-2-(3-cyanobenzenesulphonyl)aminoethyl-N-methyl-1-(3-pyridyl)cyclohexane carbothioamide, m.p. 85°–90° C., in the form of a foam;

(±)-trans-2-(3-benzenesulphonyl)aminomethyl-N-methyl-1-(3-pyridyl)cyclohexane carbothioamide, m.p. 79°–80° C., in the form of a foam;

(±)-trans-2-(isopropylsulphonyl)aminoethyl-N-methyl-1-(3-pyridyl)cyclohexane carbothioamide, m.p. 64°–65° C., in the form of a foam;

(±)-trans-2-(4-fluorobenzenesulphonyl)aminoethyl-N-ethyl-1-(3-pyridyl)cyclohexane carbothioamide, m.p. 81°–83° C., in the form of a foam;

(±)-trans-2-(3-pyridinesulphonylaminoethyl-N-ethyl-1-(3-pyridyl)cyclohexane carbothioamide, m.p. 58°–60° C., in the form of a foam;

(−)-trans-2-(3-pyridinesulphonyl)aminoethyl-N-methyl-1-(3-pyridyl)cyclohexane carbothioamide, m.p. 98°–99° C., $[\alpha]^D = -26°$;

(−)-trans-2-(4-fluorobenzenesulphonyl)aminoethyl-N-methyl-1-(3-pyridyl)cyclohexane carbothioamide, m.p. 64°–65° C. in the form of a foam, $[\alpha]^D = -20.6°$;

(−)-trans-2-(isopropylsulphonyl)aminoethyl-N-methyl-1-(3-pyridyl)cyclohexane carbothioamide, m.p. 90°–91° C., in the form of a foam; and (±)-trans-2-(isopropylsulphonyl)aminoethyl-N-methyl-1-(4-pyridyl)cyclohexane carbothioamide as a white solid, m.p. 146°–147° C.

REFERENCE EXAMPLE 1

To a solution of (±)-trans-2-aminoethyl-N-methyl-1-(3-pyridyl)cyclohexane carbothioamide (500 mg, 1.8 mmol) in ethanol (10 ml) was added, with stirring, dithiomethyl benzenesulphonyliminocarbonate (470 mg, 1.8 mmol) and the mixture heated at reflux for 8 hr, cooled and concentrated in vacuo to give a brown oil. The oil was purified by flash chromatography over silica gel using ethyl acetate/methanol (95:5) as eluent to give a pale yellow oil which was triturated with ether to give (±)-trans-2-(2-(N-benzenesulphonyl-S-methylisothioureido)ethyl)-N-methyl-1-(3-pyridyl)cyclohexane carbothioamide (280 mg), as a white solid

[N.M.R.(CDCl$_3$): 1.0–1.8 (m, 8H), 2.0–2.2 (m, 2H), (s, 3H), 2.6 (m, 1H), 3.1(d, 3H), 3.2–3.3 (m, 2H), 7.2 (m, 2H), 7.4–7.5 (m, 3H), 7.8–8.0 (dd, 2H), 8.5 (d, 1H), 8.6(d, 1H), 8.1 (br s, 1H)

Found: C, 55.9; H, 6.2; N, 11.2; S, 18.5%
$C_{23}H_{30}N_4O_2S_3$ requires: C, 56.3; H, 6.2; N, 11.4; S, 19.6%].

REFERENCE EXAMPLE 2

To a solution of (±)-trans-2-aminoethyl-N-methyl-1-(3-pyridyl)cyclohexane carbothioamide (500 mg, 1.8 mmol) in ethanol (10 ml) was added, with stirring, dithiomethyl methanesulphonyliminocarbonate (360 mg, 1.8 mmol) and the mixture heated at reflux for 8 hr, cooled and concentrated in vacuo to an oil. The oil was purified by flash chromatography over silica gel using ethyl acetate/methanol (95:5) as eluent to give (±)-trans-2-(2-N-methanesulphonyl-S-methylisothioureido)ethyl-N-methyl-1-(3-pyridyl)cyclohexane carbothioamide (220 mg), as a white solid, m. pt 74°–75° C.

[N.M.R.(CDCl$_3$): 1.3–1.8 (m, 7H), 2.0–2.2 (m, 2H), 2.4 (s, 3H), 2.6(m, 1H), 3.0 (s, 3H), 3.05(m, 1H), 3.15 (d, 3H), 3.25 (m, 2H), 7.3 (q, 1H), 7.4 (br s, 1H), 7.8 (br s, 1H), 7.9 (d, 1H), 8.5 (d, 1H), 8.6 (d, 1H)

Found: C, 49.9; H, 6.5; N, 12.6; S, 20.7%
$C_{18}H_{28}N_4O_2S_3$ requires: C, 50.4; H, 6.6; N, 13.11; S, 22.4%].

REFERENCE EXAMPLE 3

A solution of (±)-trans-2-cyanomethyl-N-methyl-1-(pyrid-3-yl)cyclohexane carbothioamide (3 g, 10.8 mmol) in dry tetrahydrofuran (30 ml) was added dropwise at room temperature under argon to a stirred suspension of lithium aluminium hydride (1.25 g, 33 mmol) in dry tetrahydrofuran (75 ml). After the addition, the mixture was stirred at reflux for 1 hr, cooled and treated with Rochelle salt solution (20 ml) and ethyl acetate (50 ml). The layers were separated and the aqueous was extracted with ethyl acetate (30 ml). The combined extracts were washed with water, dried (MgSO$_4$) and concentrated in vacuo to give a yellow oil which was triturated with ether to give (±)-trans-2-(2-aminoethyl)-N-methyl-1-(pyrid-3-yl)cyclohexane carbothioamide (2 g) as a yellow solid;

[N.M.R. (CDCl$_3$): 1.0–1.1 (m, 1H), 1.4–1.8 (m, 4H), 2.0 (m, 1H), 2.1 (m, 1H), 2.5 (m, 2H), 2.7 (m, 4H), 3.1 (d, 3H), 3.15–3.3 (m, 2H), 7.25 (q, 1H), 7.9 (dt, 1H), 8.4 (dd, 1H), 8.7 (d, 1H)].

REFERENCE EXAMPLE 4

A suspension of lithium aluminium hydride (135 mg, 3.54 mmol) at room temperature in dry tetrahydrofuran (20 ml) was treated dropwise with a dry tetrahydrofuran solution (10 ml) of 2-cyanomethylene-N-methyl-1-(pyrid-3-yl)cyclohexane carbothioamide (960 mg, 3.54 mmol). The mixture was stirred at room temperature for 10 mins. Water (5 ml) was added dropwise followed by ethyl acetate (50 ml). The mixture was washed with an aqueous solution of Rochelle salt (50 ml) and the separated organic extract dried over magnesium sulphate. Concentration in vacuo yielded a yellow gum which was purified by flash chromatography over silica gel, eluting with ethyl acetate to yield a pale yellow gum (610 mg, 2.23 mmol). Trituration with ether/hexane yielded (±)-trans-2-cyanomethyl-N-methyl-1-(pyrid-3-yl)cyclohexane carbothioamide (610 mg, 2.23 mmol), as a white solid, m.p. 177°–178° C.;

[N.M.R. (CDCl$_3$): 1.38–2.6 (c, 10H), 3.08–3.14 (d, 3H), 3.64–3.80 (m, 1H), 7.28–7.36 (m, 1H), 7.48–7.68 (br s, 1H), 7.72–8.00 (m, 1H), 8.52–8.60 (m, 1H)

Found: C, 65.5; H, 6.9; N, 15.1%
Calculated for $C_{15}H_{19}N_3S$: C, 65.9; H, 7.0; N, 15.4%
m/z=274].

REFERENCE EXAMPLE 5

A solution of diethyl cyanomethylphosphonate (215 mg, 1.2 mmol) at room temperature in dry tetrahydrofuran (20 ml) was treated with a 60% oil dispersion of sodium hydride (40 mg, 1 mmol). After 15 mins at room temperature (±)-N-methyl-2-oxo-1-(pyrid-3-yl)cyclohexane carbothioamide (245 mg, 1 mmol) was added and the resulting solution stirred for 3 hours at room temperature. Ethyl acetate (50 ml) and then water (50 ml) were added to the reaction mixture. The layers were separated and the organics washed with water (50 ml). The organic extract was dried over magnesium sulphate and concentrated in vacuo to give a crude gum. Purification by flash chromatography, eluting with a 1:1 (v/v) mixture of ethyl acetate/hexane gave (±)-2-cyanomethylene-N-methyl-1-(pyrid-3-yl)cyclohexane carbothioamide as a colourless gum (190 mg, 0.7 mmol). Trituration with ether yielded a white solid (190 mg, 0.7 mmol), m.p. 182°183° C.;

[N.M.R. (CDCl$_3$): 1.47–1.78 (c, 2H), 1.78–2.00 (c, 2H), 2.20–2.38 (m, 1H), 2.46–2.64 (m, 1H), 2.82–2.96 (m, 1H), 3.06–3.24 (m, 1H), 3.22–3.26 (d, 3H), 3.94 (s, 1H), 7.26–7.36 (m, 1H), 7.48–7.64 (m, 2H), 8.48–8.52 (m, 1H), 8.52–8.58 (m, 1H)

Found: C, 66.6; H, 6.3; N, 15.7%
$C_{15}H_{17}N_3S$: C, 66.4; H, 6.3; N, 15.5%
m/z=271].

REFERENCE EXAMPLE 6

A vigorously stirred solution of (±)-2-(pyrid-3-yl)cyclohexanone (5.5 g, 30 mmol) in anhydrous tetrahydrofuran (50 ml) under argon at −15° C. was treated with potassium t-butoxide (3.36 g, 30 mmol).

After 60 minutes at 0° C., a solution of methyl isothiocyanate (2.4 g, 33 mmol) in anhydrous tetrahydrofuran (10 ml) was added during 5 minutes. After 2.5 hours at 0° C. the solution was warmed to 20° C. and then poured into a saturated aqueous brine solution (250 ml). The mixture was extracted with ethyl acetate (50 ml) and then with chloroform (3×50 ml). The combined organic extracts were dried over sodium sulphate and the concentrated in vacuo (30° C.; 14 mmHg).

The crude product was recrystallised from methanol to give (±)-N-methyl-2-oxo-1-(pyrid-3-yl)cyclohexane carbothioamide (4.8 g, 19 mmol), m.p. 188°–190° C.;

[N.M.R. (CDCl$_3$): 1.62–2.06 (m, 4H), 2.42–2.60 (m, 2H), 2.60–2.82 (m, 1H), 2.84–3.06 (m, 1H), 3.16–3.2 (d, 3H), 7.24–7.34 (ddd, 1H), 7.6–7.68 (ddd, 1H), 8.43–8.47 (d, 1H), 8.48–854 (dd, 1H), 8.9–9.2 (br s, 1H)

Found: C, 62.9; H, 6.6; N, 11.3; S, 13.1%

Calculated for C$_{13}$H$_{16}$N$_2$OS: C, 62.9; H, 6.5; N, 11.3; S, 12.9%].

REFERENCE EXAMPLE 7

A solution of (±)-trans-1-[(pyrid-3-yl)bromomethyl]-cyclopentanol (10.24 g, 40 mmol) in anhydrous tetrahydrofuran (500 ml) at 0° C. was treated, dropwise during 30 minutes, with a solution of silver perchlorate (9.9 g, 48 mmol) in anhydrous tetrahydrofuran (50 ml). After 60 minutes at 0° C. the mixture was poured into a mixture of saturated aqueous brine solution (500 ml) and 10% v/v aqueous sodium bicarbonate solution (500 ml). The resulting mixture was filtered and then extracted with ethyl acetate (2×500 ml). The combined organic extracts were washed with brine and then dried over sodium sulphate. Concentration in vacuo (30° C.; 14 mmHg) afforded a crude oil which was recrystallised from cyclohexane (120 ml) to give (±)-2-(pyrid-3-yl)-cyclohexane (6.7 g, 38 mmol), m.p. 78°–80° C.

[N.M.R. (CDCl$_3$): 1.72–2.12 (m, 4H), 2.12–2.40 (m, 2H), 2.40–2.64 (m, 2H), 3.56–3.72 (dd, 1H), 7.22–7.32 (m, 1H), 7.44–7.54 (ddd, 1H), 8.34–8.42 (dd, 1H), 8.46–8.54 (dd, 1H)].

REFERENCE EXAMPLE 8

A solution of 3-cyclopentylidenemethylpyridine (62.2 g, 0.39 mol) in acetone (600 ml) and water (100 ml) was treated with a solution of concentrated sulphuric acid (18.9 g, 0.19 mmol) in water (100 ml) at 5° C. The ice-cold solution was treated with 1,3-dibromo-5,5-dimethylhydantoin (55 g, 0.19 mol) during 20 minutes. After 3.5 hours at 0° C. the mixture was treated with sodium bicarbonate (33.6 g, 0.4 mol) followed by water (2 l) and then extracted with ethyl acetate (2×500 ml). The organic phase was removed and washed with 10% w/v aqueous sodium bicarbonate solution (500 ml) followed by water (200 ml) and brine (200 ml). The crude extract was dried over sodium sulphate and then filtered through a column of flash silica gel (10 cm×2.4 cm diameter). After concentration in vacuo (20° C.; 14 mmHg) the dark oil crystallised on standing to give (±)-trans-1-[(pyrid-3-yl)bromomethyl]cyclopentanol (56 g, 0.22 mol) m.p. 92°–94° C.

[N.M.R. (CDCl$_3$) 1.36–2.06 (c, 8H), 2.32–2.46(br s, 1H), 5.02 (s, 1H), 7.24–7.34 (ddd, 1H), 8.0–8.1 (ddd, 1H), 8.52–8.56 (dd, 1H), 8.62–8.66 (d, 1H)

Found: C, 51.9; H, 5.6; Br, 30.6; N, 5.5%

Calculated for C$_{11}$H$_{14}$BrNO: C, 51.6; H, 5.5; Br, 31.2; N, 5.5%].

REFERENCE EXAMPLE 9

A suspension of cyclopentyltriphenylphosphonium bromide (226 g, 0.55 mol) in anhydrous tetrahydrofuran (1000 ml) at 2° C. was treated with vigorous stirring under an atmosphere of argon, with potassium t-butoxide (61.7 g, 0.55 mol). The dark red mixture was stirred at 5° C. for 80 minutes and then treated with pyridine-3-carbaldehyde (58.9 g, 0.55 mol) during a period of 20 minutes. The reaction mixture was stirred at 0° C. for 2 hours and then at 20° C. for 18 hours. The tetrahydrofuran was removed in vacuo (30° C.; 14 mmHg) and the residue extracted with pentane (2×500 ml). After treatment with decolourising charcoal (5 g), the mixture was filtered through a plug of flash silica gel (Merck 70–230 mesh; 13 cm×2 cm diameter). The filtrate was concentrated in vacuo (30° C., 14 mmHg; then 20° C., 0.01 mmHg) to afford 3-cyclopentylidenemethylpyridine (54 g, 0.34 mol) as an orange oil which was used without further purification;

[N.M.R. (CDCl$_3$): 1.6–1.95 (m, 4H), 2.4–2.65 (m, 4H), 6.26–6.34 (m, 1H), 7.16–7.25 (ddd, 1H), 7.56–7.65 (ddd, 1H), 8.52–8.52 (d, 1H)].

REFERENCE EXAMPLE 10

A 4:1 mixture of (±)-cis/trans-2-methoxy-1-(pyrid-3-yl)cyclohexanol (2 g, 10 mmol), toluene and phosphorus pentoxide (3.4 g, 24 mmol) was heated at reflux for 5 hours. The mixture was then filtered and the precipitate partitioned between 2M sodium hydroxide solution (80 ml) and diethyl ether (25 ml). The aqueous layer was extracted with ether (3×25 ml) and the combined organic extracts were dried over sodium sulphate. Concentration in vacuo afforded a crude oil which was purified by flash chromatography to give 2-(pyrid-3-yl)cyclohexanone (0.7 g, 4 mmol).

REFERENCE EXAMPLE 11

To a solution of 2.5M n-butyllithium in hexane (13.2 ml, 33 mmol) at −78° C. was added diethyl ether (15 ml) followed by a solution of 3-bromopyridine (4.7 g, 30 mmol) in ether (90 ml) over a period of 10 minutes. After 1 hour at −78° C. a solution of (±)-2-methoxycyclohexanone (3.84 g, 30 mmol) in ether (20 ml) was added dropwise during 10 minutes. After 2 hours at −78° C. and 30 minutes at 0° C. the reaction mixture was warmed to 20° C. and then poured onto ice (150 g). The mixture was extracted with ether (2×50 ml) and then the combined organic extracts were extracted with 1N hydrochloric acid (50 ml). This aqueous extract was washed with ether (20 ml) and then treated with 2M sodium hydroxide solution (25 ml) and extracted with ether (3×100 ml). The organic extracts were combined, washed with brine then dried over anhydrous sodium sulphate. Concentration in vacuo afforded (±)-2-methoxy-1-(pyrid-3-yl)cyclohexanol (5.0 g, 24 mmol) as a 4:1 mixture of cis and trans isomers;

[N.M.R. (CDCl$_3$): 1.2–2.14 (c), 2.24–2.44 (m), 2.90–3.28 (c), 3.48–3.60 (m), 7.18–7.30 (m), 7.78–7.96 (m), 8.40–8.48 (m), 8.62–8.72 (m), 8.78–8.82 (m)].

The present invention includes within its scope pharmaceutical compositions which comprise a compound of general formula (I) or a pharmaceutically acceptable salt thereof, in association with a pharmaceutically acceptable carrier or coating. In clinical practice the compounds of the present invention may be administered rectally, but are preferably administered parenterally, by inhalation if appropriate, or, more preferably, orally.

Solid compositions for oral administration include compressed tablets, pills, powders and granules. In such solid compositions, one or more of the active compounds is, or are, admixed with at least one inert diluent such as starch, sucrose or lactose.

The compositions may also comprise, as is normal practice, additional substances other than inert diluents, e.g. lubricating agents, such as magnesium stearate.

Liquid compositions for oral administration include pharmaceutically acceptable emulsions, inert diluents commonly used in the art such as water and liquid paraffin. Besides inert diluents such compositions may comprise adjuvants, such as wetting, and suspending agents, and sweetening, flavouring, perfuming and preserving agents. The compositions according to the invention for oral administration also include capsules of absorbable material such as gelatin, containing one or more of the active substances with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive and injectable organic esters such as ethyl oleate. The compositions may also contain adjuvants such as stabilising, preserving, wetting, emulsifying and dispersing agents. They may be sterilised by, for example, filtration through a bacteria-retaining filter, by incorporation in the compositions of sterilising agents, by irradiation or by heating. They may also be manufactured in the form of sterile solid compositions, which can be dissolved in sterile water or some other sterile injectable medium immediately before use.

Compositions for inhalation may be sterile aqueous solutions which are then nebulised or dry powders formulated in accordance with known methods.

Solid compositions for rectal administration include suppositories formulated in accordance with known methods and containing one or more of the compounds of formula (I) or a pharmaceutically acceptable salt thereof.

The percentage of active ingredient in the composition of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration, the duration of the treatment, and the condition of the patient. In the adult, the doses are generally from about 0.001 to about 50, preferably from about 0.01 to about 5, mg/kg body weight per day by oral administration. By inhalation, either as a nebulised solution or as a formulated dry powder, the preferred daily dosage is from about 0.001 to about 5, preferably from about 0.01 to about 0.5, mg/kg body weight.

The following Example illustrates pharmaceutical compositions according to the present invention.

COMPOSITION EXAMPLE

No. 2 size gelatin capsules each containing:

| | |
|---|---|
| (±)-trans-2-benzenesulphonylaminoethyl-N-methyl-1-(3-pyridyl)cyclohexane carbothioamide | 20 mg |
| lactose | 100 mg |
| starch | 60 mg |
| dextrin | 40 mg |
| magnesium stearate | 1 mg | were prepared in accordance with the usual procedure.

We claim:

1. A thioformamide compound of formula (I):

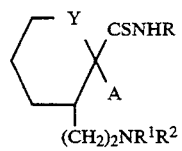

in which R represents an alkyl group;

A is (1) a phenyl group, which is unsubstituted or substituted by one or more substituents selected from a halogen atom and a cyano, nitro, trifluoromethyl, carbamoyl, carboxyl, alkoxycarbonyl and alkylsulphonyl group, or (2) a heterocyclyl group selected from pyrid-3-yl, pyrid-4-yl, indol-3-yl and thiazol-5-yl, which is unsubstituted or substituted by an alkyl or alkoxy group or a halogen atom;

Y represents an ethylene or methylene group or a direct bond; and either:

(1) $R^1$ represents hydrogen and $R^2$ represents:
  i) a group of formula —$CXNHR^3$, wherein $R^3$ is an alkyl group and X is a group of formula =$NSO_2R^4$, wherein $R^4$ is an alkyl or phenyl group; or
  ii) a group of formula —$SO_2R^5$, wherein $R^5$ is:
    (a) a naphthyl or phenyl group optionally substituted by one or more halogen atoms, hydroxy, alkoxy, $C_{3-6}$ cycloalkoxy, alkyl, $C_{2-4}$ alkenyl, cyano, nitro, trifluoromethyl, carboxy, alkoxycarbonyl, amino, alkylamino, dialkylamino, alkoxycarbonylamino, alkanoylamino, dialkanoylamino, benzoylamino, carbamoyl, N-(optionally hydroxyalkyl)carbamoyl or N,N-di(optionally hydroxyalkyl)carbamoyl groups, or amino or carbamoyl groups N,N-disubstituted by a $C_{3-6}$ alkylene chain, one or more of whose methylene groups may have been replaced by an oxygen or sulphur atom or an imino or alkylimino group;
    (b) a pyridyl or thienyl group; or
    (c) an alkyl group optionally substituted by one or more halogen atoms, phenyl, naphthyl, pyridyl, hydroxy, alkoxy, $C_{3-6}$ cycloalkoxy, alkyl, $C_{2-4}$ alkenyl, cyano, nitro, trifluoromethyl, carboxy, alkoxycarbonyl, amino, alkylamino, dialkylamino, alkoxycarbonylamino, alkanoylamino, dialkanoylamino, benzoylamino, carbamoyl, N-(optionally hydroxyalkyl)carbamoyl or N,N-di(optionally hydroxyalkyl)carbamoyl groups, or amino or carbamoyl groups N,N-disubstituted by a $C_{3-6}$ alkylene chain, one or more of whose methylene groups may have been replaced by an oxygen or sulphur atom or an imino or alkylimino group; or (2) $R^1$ and $R^2$ both independently represent a group of formula —$SO_2R^5$, as defined above;

wherein all the alkyl groups or moieties are straight-chain or branched and contain 1 to 6 carbon atoms and provided that at least one of A or $R^5$ is pyridyl; or a salt thereof.

2. A compound according to claim 1 in which:
  i) R represents a methyl or ethyl group;
  ii) A represents a pyrid-3-yl or pyrid-4-yl group;
  iii) Y represents a methylene group;
  iv) $R^1$ represents a hydrogen atom;
  v) $R^3$ represents a methyl group;
  vi) $R^4$ represents a methyl or phenyl group; and vii) $R^5$ represents:
   a) a phenyl or naphthyl group optionally substituted by one or more halogen atoms or nitro, cyano, alkoxy or dialkylamino groups;
   b) a pyrid-3-yl or thien-2-yl group; or
   c) an alkyl group of up to 4 carbon atoms.

3. A compound according to claim in which $R^5$ represents:
   a) a phenyl or 1-naphthyl group optionally substituted by one or more fluorine or chlorine atoms or nitro, cyano, methoxy or dimethylamino groups;
   b) a pyrid-3-yl or thien-2-yl group; or
   c) a methyl group.

4. A compound according to claim 1 which is selected from the group consisting of:
   (±)-trans-2-(N-methyl-N′-benzenesulphonyliminoureido)ethyl-N-methyl-1-(3-pyridyl)cyclohexane carbothioamide,
   (±)-trans-2-(N-methyl-N′-methanesulphonyliminoureido)ethyl-N-methyl-1-(3-pyridyl)cyclohexanecarbothioamide,
   (±)-trans-2-benzenesulphonylaminoethyl-N-methyl-1-(3-pyridyl)cyclohexane carbothioamide,
   (±)-trans-2-methanesulphonylaminoethyl-N-methyl-1-(3-pyridyl)cyclohexane carbothioamide,
   (±)-trans-2-(4-fluorobenzenesulphonyl)amino-ethyl-N-methyl-1-(3-pyridyl)cyclohexane carbothioamide,
   (±)-trans-2-(4-nitrobenzenesulphonyl)amino-ethyl-N-methyl-1-(3-pyridyl)cyclohexane carbothioamide,
   (±)-trans-2-(4-chlorobenzenesulphonyl)amino-ethyl-N-methyl-1-(3-pyridyl)cyclohexane carbothioamide,
   (±)-trans-2-(4-methoxylbenzenesulphonyl)aminoethyl-N-methyl-1-(3-pyridyl)cyclohexane carbothioamide,
   (±)-trans-2-(2-thiophenesulphonyl)aminoethyl-N-methyl-1-(3-pyridyl)cyclohexane carbothioamide,
   (±)-trans-2-(3-pyridinesulphonyl)aminoethyl-N-methyl-1-(3-pyridyl)cyclohexane carbothioamide,
   (±)-trans-2-(3,4-difluorobenzenesulphonyl)aminoethyl-N-methyl-1-(3-pyridyl)cyclohexane carbothioamide,
   (±)-trans-2-(5-dimethylamino-1-naphthalene-sulphonyl)aminoethyl-N-methyl-1-(3-pyridyl)-cyclohexane carbothioamide,
   (±)-trans-2-(propylsulphonyl)aminoethyl-N-methyl-1-(3-pyridyl)cyclohexane carbothioamide,
   (±)-trans-2-(isopropylsulphonyl)aminoethyl-N-methyl-1-(3-pyridyl)cyclohexane carbothioamide,
   (±)-trans-2-(butylsulphonyl)aminoethyl-N-methyl-1-(3-pyridyl)cyclohexane carbothioamide,
   (±)-trans-2-(2-fluorobenzenesulphonyl)amino-ethyl-N-methyl-1-(3-pyridyl)cyclohexane carbothioamide,
   (±)-trans-2-(3-cyanobenzenesulphonyl)aminoethyl-N-methyl-1-(3-pyridyl)cyclohexane carbothioamide,
   (±)-trans-2-(benzenesulphonyl)aminoethyl-N-ethyl-1-(3-pyridyl)cyclohexane carbothioamide,
   (±)-trans-2-(isopropylsulphonyl)aminoethyl-N-ethyl-1-(3-pyridyl)cyclohexane carbothioamide,
   (±)-trans-2-(4-fluorobenzenesulphonyl)amino-ethyl-N-ethyl-1-(3-pyridyl)cyclohexane carbothioamide,
   (±)-trans-2-(3-pyridinesulphonylaminoethyl-N-ethyl-1-(3-pyridyl)cyclohexane carbothioamide,
   (±)-trans-2-(3-pyridinesulphonyl)aminoethyl-N-methyl-1-(3-pyridyl)cyclohexane carbothioamide,
   (±)-trans-2-(4-fluorobenzenesulphonyl)amino-ethyl-N-methyl-1-(3-pyridyl)cyclohexane carbothioamide,
   (±)-trans-2-(isopropylsulphonyl)aminoethyl-N-methyl-1-(3-pyridyl)cyclohexane carbothioamide,
   (±)-trans-2-(isopropylsulphonyl)aminoethyl-N-methyl-1-(4-pyridyl)cyclohexane carbothioamide,
   and pharmaceutically acceptable salts thereof.

5. A pharmaceutical composition comprising a compound of claim 1 in association with a pharmaceutically acceptable carrier or diluent.

6. A method for the treatment of a disorder associated with vascular, respiratory, gastrointestinal tract, urinary bladder or uterus smooth muscle contraction in a patient which method comprises administering to the patient an amount effective to combat said disorder of a compound as claimed in claim 1.

* * * * *